United States Patent
Zander et al.

(10) Patent No.: US 12,426,901 B2
(45) Date of Patent: Sep. 30, 2025

(54) PLATE TO NAIL ALIGNMENT PIN/K-WIRE

(71) Applicant: Stryker European Operations Limited, Carrigtwohill (IE)

(72) Inventors: Nils Zander, Eckernförde (DE); Manfred Wieland, Kiel (DE); Hendrik Kluever, Schoenkirchen (DE)

(73) Assignee: Stryker European Operations Limited, Carrigtwohill (IE)

( * ) Notice: Subject to any disclaimer, the term of this patent is extended or adjusted under 35 U.S.C. 154(b) by 132 days.

(21) Appl. No.: 18/522,638

(22) Filed: Nov. 29, 2023

(65) Prior Publication Data
US 2024/0173041 A1    May 30, 2024

Related U.S. Application Data

(60) Provisional application No. 63/428,453, filed on Nov. 29, 2022.

(51) Int. Cl.
*A61B 17/17* (2006.01)
*A61B 17/56* (2006.01)

(52) U.S. Cl.
CPC ...... *A61B 17/1725* (2013.01); *A61B 17/1796* (2013.01); *A61B 2017/564* (2013.01)

(58) Field of Classification Search
CPC .............. A61B 17/1725; A61B 17/1796
See application file for complete search history.

(56) References Cited

U.S. PATENT DOCUMENTS

| | | | |
|---|---|---|---|
| 2,489,870 A | 11/1949 | Dzus | |
| 9,649,118 B2 | 5/2017 | Mebarak | |
| 9,907,597 B2 | 3/2018 | Kollmer | |
| 10,085,781 B2 | 10/2018 | Zander et al. | |
| 10,792,082 B2 | 10/2020 | Zander et al. | |
| 10,874,520 B2 | 12/2020 | Segina et al. | |
| 11,039,865 B2 | 6/2021 | Singh et al. | |
| 11,350,976 B2 | 6/2022 | Spreiter et al. | |
| 11,471,200 B2 | 10/2022 | Spreiter et al. | |
| 11,478,277 B2 | 10/2022 | Aebi et al. | |
| 2002/0183750 A1* | 12/2002 | Buhler | A61B 17/1725 606/62 |
| 2003/0105461 A1* | 6/2003 | Putnam | A61B 17/8033 606/104 |
| 2006/0084999 A1* | 4/2006 | Aschmann | A61B 17/744 606/64 |
| 2007/0005065 A1* | 1/2007 | Fernandez Dell'Oca | A61B 17/1725 606/62 |

(Continued)

OTHER PUBLICATIONS

Masada, Kendall M., et al., "Trauma Tips & Tricks: Nail Plate Combination Fixation for Distal Femur Fractures", Department of Orthopaedic Surgery, University of Pennsylvania, vol. 30, Jun. 2020. 4 pgs.

*Primary Examiner* — Christian A Sevilla
(74) *Attorney, Agent, or Firm* — Lerner David LLP

(57) ABSTRACT

A method for aligning an aiming block with respect to a bone includes driving a bone screw into a bone to pass a tip of the bone screw through a hole of an intramedullary nail and to anchor a head of the bone screw in a cortical region of the bone; inserting a pin extending from a surface of an aiming block through a hole of a bone plate; and contacting the pin against the head of the bone screw to align the hole of the bone plate with the head of the bone screw.

20 Claims, 7 Drawing Sheets

(56) References Cited

U.S. PATENT DOCUMENTS

| | | |
|---|---|---|
| 2011/0224736 A1* | 9/2011 | Humphrey .......... A61B 17/8057 |
| | | 606/289 |
| 2013/0079829 A1 | 3/2013 | Globerman et al. |
| 2013/0289626 A1 | 10/2013 | Murashko, Jr. |
| 2015/0105779 A1 | 4/2015 | Smith et al. |
| 2016/0220286 A1 | 8/2016 | Garvey et al. |
| 2016/0374738 A1 | 12/2016 | Smith et al. |
| 2018/0000496 A1 | 1/2018 | Langdale et al. |

* cited by examiner

PLATE TO NAIL ALIGNMENT PIN/K-WIRE

CROSS-REFERENCE TO RELATED APPLICATIONS

The present application claims priority to U.S. provisional application No. 63/428,453 filed Nov. 29, 2022, the disclosure of which is incorporated by reference herein.

BACKGROUND OF THE INVENTION

The present disclosure generally relates to a fracture fixation system, instrumentation and method of use used in the fixation of fractures of bones such as the femur, tibia, humerus and radius, including periarticular fractures. More specifically, the present invention encompasses an aiming block fixation system that aids in the location of bone screws and drilling of pilot holes for the placement and intraoperative adjustment and fixation of the plate to the fractured bone.

Typical fixation of a fracture of a long bone with a bone plate requires making an incision in the tissue, reducing the fracture, placing a bone plate on the fractured bone, and securing the bone plate to the bone with fixation elements such as screws. The bone plate immobilizes the fracture to allow the fracture to heal.

Typically, bone plates have a bone-contacting surface and an opposing surface with a plurality of holes or apertures extending between the two surfaces. These holes or apertures may be either threaded (for fixing the plate to the bone with locking screws) or non-threaded (for fixing the plate to the bone with regular screws) and may be circular or oblong in shape.

Such threaded screws are driven into the bone tissue after so-called pre-drilled or pilot-drilled holes have been generated in the bone tissue. These pre-drilled holes allow for a reliable screw insertion, and they reduce the risk of further damaging the bone when the screw is inserted.

In order to facilitate the drilling of these pre-drilled holes, there are known so-called aiming or targeting devices, which work like a drilling jig. Thereby, an aiming or targeting device is detachably fixed to the metal bone plate in a precise position.

Some types of bone plates, however, do not include holes in a location that would accommodate the use of aiming or targeting devices. There thus exists a need for a system that will align a surgical tool (e.g., drill bit) with a hole of a bone plate. The present invention addresses this problem and others by providing an aiming block which has bores for aligning surgical tools, whose arrangement matches or corresponds to the arrangement of holes of a particular bone plate type.

BRIEF SUMMARY OF THE INVENTION

In one aspect, a method for aligning an aiming block with respect to a bone comprises: driving a bone screw into a bone to pass a tip of the bone screw through a hole of an intramedullary nail and to anchor a head of the bone screw in a cortical region of the bone; inserting a pin extending from a surface of an aiming block through a hole of a bone plate; and contacting the pin against the head of the bone screw to align the hole of the bone plate with the head of the bone screw.

In another aspect, the method further comprises inserting the intramedullary nail into a medullary canal of a bone.

In a different aspect, the contacting step includes inserting the pin into a recess within the head of the bone screw.

In a further aspect, the contacting step further comprises pressing the pin partially into the aiming block by compressing a spring disposed between the pin and aiming block.

In a different aspect, the method further comprises driving a second bone screw into the bone to pass a tip of the second bone screw through a second hole of the intramedullary nail and to anchor a head of the second bone screw in the cortical region of the bone.

In another aspect, the method further comprises inserting a second pin extending from the inner surface of the aiming block through a second hole of the bone plate.

In a different aspect, the contacting step includes placing the pin against the head of the bone screw and the second pin against the head of the second bone screw.

In another aspect, the driving step includes driving the head of the bone screw into a countersunk recess within the bone.

In another aspect of the present disclosure, a method of aligning an aiming block with respect to a bone comprises: drilling a hole in a cortical region of a bone; inserting a pin extending from a surface of an aiming block through a hole of a bone plate; and locating the pin within the hole in the cortical region of the bone.

In a different aspect, the method further comprises inserting an intramedullary nail into a medullary canal of the bone.

In another method, the locating step includes locating the pin such that a central longitudinal axis of the pin aligns with a central longitudinal axis of a hole of the intramedullary nail.

In a further aspect, the method further comprises removing the bone plate and the aiming block from the bone.

In another aspect, the method further comprises inserting a bone screw through the bone such that a head of the bone screw sits in a recess formed by the pin and a tip of the bone screw extends through the hole of the intramedullary nail.

In a different aspect, the method further comprises placing the bone plate over the bone such that the head of the bone screw sits beneath the hole of the bone plate.

According to another aspect of the present disclosure, a method for aligning an aiming block with respect to a bone comprises: inserting an intramedullary nail into a medullary canal of a bone; inserting a k-wire into the bone and through a hole of the intramedullary nail; placing a hole of a bone plate and an aligned hole extending through an aiming block over an end of the k-wire; and guiding the bone plate and the aiming block along the k-wire to contact an inner surface of the bone plate to the bone.

In another aspect, the method further comprises inserting a second k-wire into the bone and through a second hole of the intramedullary nail.

In a different aspect, the placing step further comprises placing a second hole of the bone plate and an aligned second hole extending through the aiming block over an end of the second k-wire.

In yet another aspect, the guiding step includes guiding the bone plate and the aiming block along the k-wire and the second k-wire to contact the inner surface of the bone plate to the bone.

In a further aspect, the method further comprises inserting a cannulated bone screw into the bone to pass a tip of the cannulated bone screw through the hole of the intramedullary nail and to anchor a head of the cannulated bone screw into a cortical region of the bone.

In a different aspect, the step of inserting the k-wire includes inserting the k-wire through the cannulated bone screw.

According to another aspect of the present disclosure, a system for aligning an aiming block comprises: an intramedullary nail insertable within a medullary canal of a bone; a bone plate including an inner bone-contacting surface, an opposing outer surface, and a hole extending through the bone plate along a plate thickness dimension measured from the inner surface to the outer surface; an aiming block including a pin extending from a lower surface of the aiming block and having a pin length measured from the lower surface of the aiming block to a terminal end of the pin, the pin of the aiming block being insertable within the hole of the bone plate, characterized in that the pin length is greater than the plate thickness.

In another aspect, the system further comprises a bone screw including a head and a shank.

In a different aspect, the head of the bone screw is configured to be sunk under an exterior surface of the bone.

In a further aspect, the inner bone-contacting surface of the bone plate is configured to be placed against the bone such that the head of the bone screw does not contact the inner bone-contacting surface of the bone plate.

In another aspect, the head of the bone screw defines a recess configured to at least partially receive the pin.

In a different aspect, the head of the bone screw is configured to be secured within the hole of the bone plate.

In yet another aspect, the shank of the bone screw is extendable through a bore of the intramedullary nail.

In a further aspect, the pin of the aiming block is insertable through the hole of the bone plate such that the pin contacts the bone.

In a different aspect, the pin of the aiming block is insertable through the hole of the bone plate such that the pin contacts the head of the bone screw.

In another aspect, the pin includes a spring configured to bias the pin away from the aiming block.

In a different aspect, the pin extends orthogonally from the lower surface of the aiming block.

In a further aspect, the aiming block further comprises a second pin insertable within a second hole of the bone plate.

In another aspect, the pin is cannulated.

In yet another aspect, the system further comprises a k-wire configured to extend through a cannulation of the pin and through the hole of the bone plate.

In a different aspect, the lower surface of the aiming block is contoured to correspond to the outer surface of the bone plate.

BRIEF DESCRIPTION OF THE DRAWINGS

The features, aspects, and advantages of the present invention will become better understood with regard to the following description, appended claims, and accompanying drawings in which:

DETAILED DESCRIPTION

As used herein, when referring to bones or other parts of the body, the term "proximal" means closer to an operator and the term "distal" means further away from the operator. The term "anterior" means toward the front of the patient's body and the term "posterior" means toward the back of the patient's body. The term "inferior" means toward the feet and the term "superior" means towards the head. The term "medial" means toward the midline of the body and the term "lateral" means away from the midline of the body.

Figure 1:
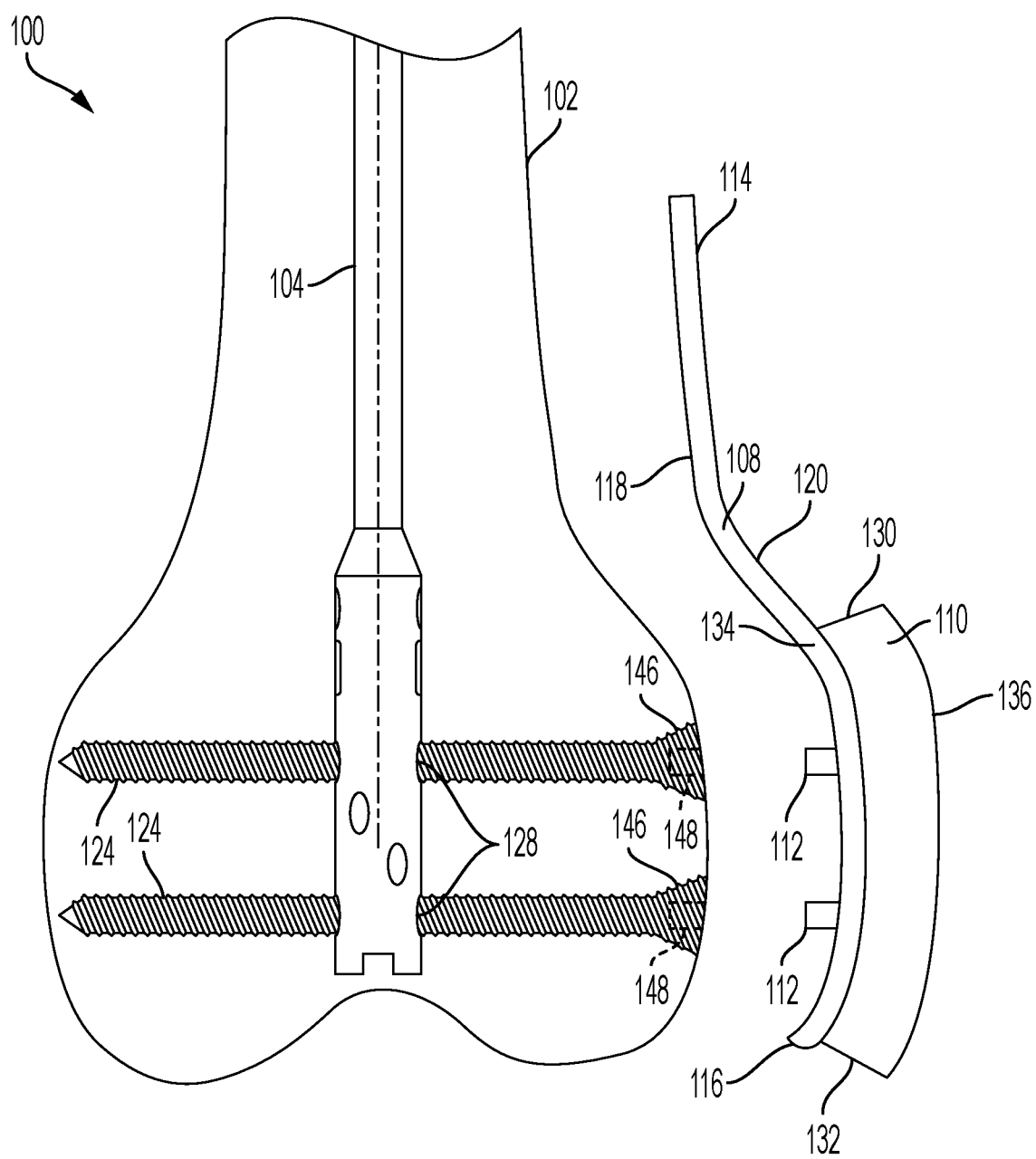
FIG. 1 is a side view of a fracture fixation system.

FIG. 1 illustrates a perspective view of fracture fixation system 100 for securing a fractured femur 102. Although the embodiments depicted herein describe and illustrate a femur, it is envisioned that the fracture fixation system 100 may be compatible with other bones, such as the tibia, humerus, and other long bones. Fracture fixation system 100 includes an elongate bone plate 108 and an elongate intramedullary nail 104. A plurality of fasteners 124 extend from a cortical region of bone through intramedullary nail 104. A targeting block 110 is removably attached to bone plate 108 via pins 112.

Figure 2:
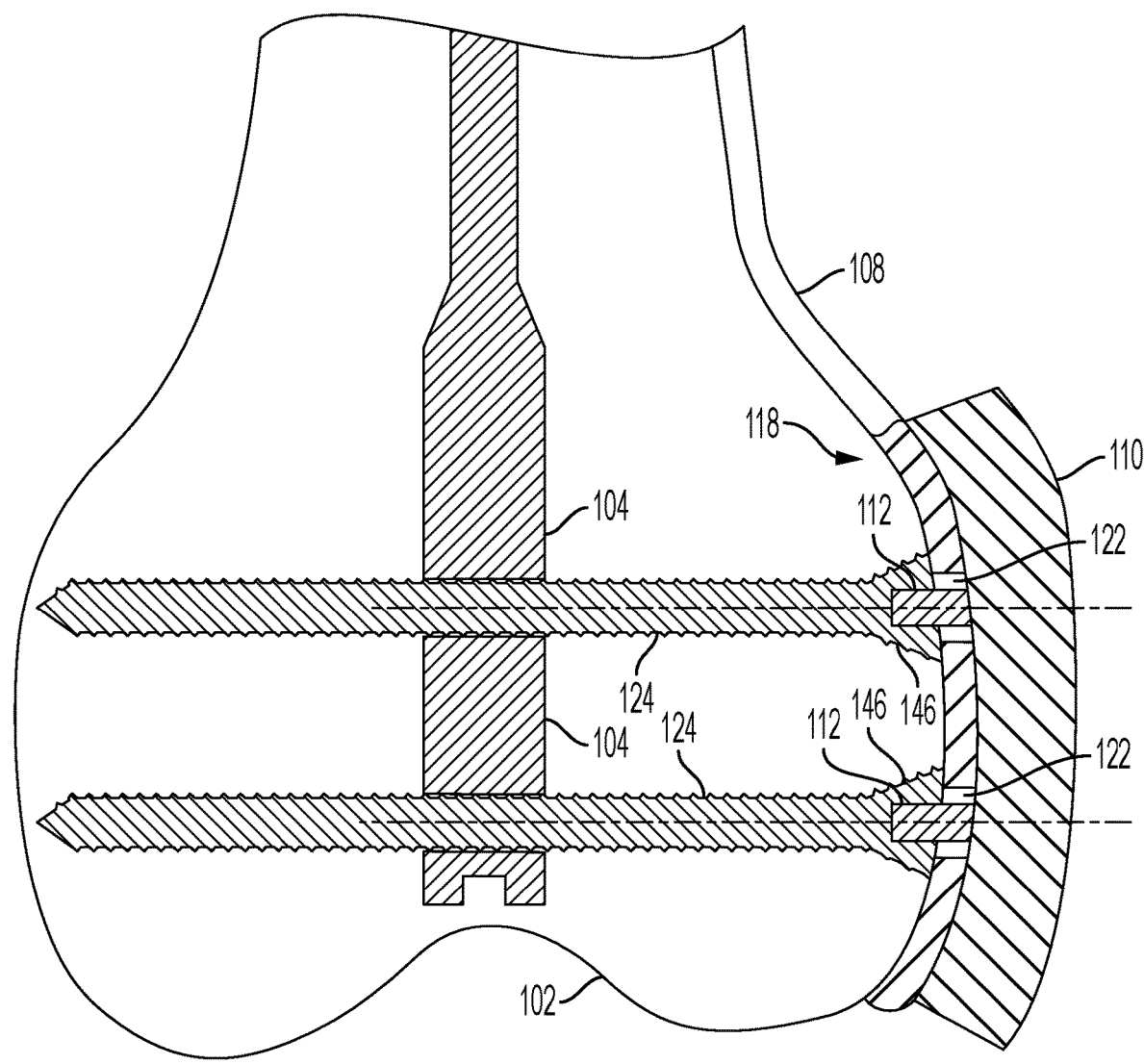
FIG. 2 is a side cross-sectional view of the fracture fixation system of FIG. 1 in an implanted configuration.

FIGS. 1-2 depict a bone plate 108 used with fracture fixation system 100 according to one embodiment of the present invention. Bone plate 108 is elongated and extends from a superior end 114 to an inferior end 116. An inner surface 118 of bone plate 108 is configured to face and contact the bone and an opposing outer surface 120 of bone plate 108 is configured to face away from the bone, e.g., in a lateral direction. Inner surface 118 may be substantially concave or otherwise shaped to contour to the underlying bone surface. The curvature of inner surface 118 may also be configured to initially define a gap between inner surface 118 and the underlying femur 102. Inner surface 118 may then flex such that the gap is closed when fasteners are driven though bone plate 108.

Inner surface 118 of bone plate 108 may be substantially smooth and lack slots, cutouts, or other regions (aside from any separate screw holes therethrough) that could accept a head of an underlying fastener. Bone plate 108 is configured to transition between an implanted configuration and a removed configuration. In an implanted configuration, such as that depicted in FIG. 2, the substantially smooth inner surface 118 is configured to sit flush or substantially flush with the underlying bone. In certain embodiments, unlinked fasteners 124, such as bone screws, are anchored into the underlying cortical bone and may sit flush with the outer cortical bone surface or be sunk beneath the cortical surface to avoid interfering with the seating of the bone plate 108 on the bone. In such a manner, the inner surface 118 of bone plate 108 may cover an aperture or a portion of an aperture in bone defined by the screw heads driven therein.

Bone plate 108 defines at least one hole 122 extending transverse to the longitudinal axis of the plate. Hole 122 preferably includes a pattern of holes spaced across bone plate 108. Different hole patterns may be implemented for different bone plates and applications throughout the body. Hole 122 is configured to receive a fastener therethrough and may also be configured to receive pin 112 therethrough. The fastener may be a bone screw, nail, beam, or other fastener type known in the art. Hole 122 may further have contouring along its internal surface to engage with the head of the fastener being driven therethrough. Such contouring may allow for fastener insertion at variable angles while maintaining a strong connection with the head of the fastener. This variable angle locking concept relies on a multi-point form-/friction-fit fixation between plate and screw. This allows for a sufficient interference fit between plate and screw, thus preventing an unintended screw back-out in-vivo. Further disclosure related to the configuration is found in U.S. Pat. No. 11,039,865, the disclosure of which is incorporated by reference herein. The curvature of bone plate 108 and the contouring of hole 122 allows each fastener to be driven into the underlying bone at optimized angles to reach and stabilize the fragmented bone. Locking features such as washers or plates may be utilized on the outer surface 120 of bone plate 108 to prevent fasteners from backing out of the bone and bone plate.

Hole 122 may be threaded or unthreaded. If hole 122 is threaded, then a fastener being driven therein may be inserted along a fixed axis, i.e., the central longitudinal axis of hole 122. Alternatively, hole 122 may be unthreaded to allow for a fastener to be driven therein along multiple axes. Hole 122 may be circular or elliptic. In some embodiments, an elliptic hole (not shown) may accept multiple fasteners, each configured for a different purpose. For example, one fastener may lock the bone plate to a first bone fragment and another fastener may compress a second bone fragment toward the first bone fragment. In other embodiments, a single fastener may be inserted at any one of multiple locations long the elliptic hole or slot.

Bone plate 108 is an elongated member formed from a single piece of rigid material, such as stainless steel, titanium, or another rigid material known in the art. The bone plate 108 may have a substantially uniform plate thickness, or it may have varying thicknesses depending on the orientation and type of fasteners extending through bone plate 108, e.g., the plate may be thicker in regions to accommodate a cross brace or support pin therethrough. Bone plate 108 may have various geometries to extend across a plurality of bones of a patient's body. For example, a femoral bone plate may be longer and straighter than a calcaneal bone plate.

Continuing with the embodiment of FIGS. 1-2, intramedullary nail 104 defines and extends along a longitudinal axis. Intramedullary nail 104 may have a circular cross-section and be inserted into a medullary canal of a patient via common insertion methods. The medullary canal contains marrow and is circumferentially encased by cortex which provides a dense outer surface that fasteners can engage with.

One or more holes 128 are defined by and extend transversely through intramedullary nail 104. The diameter of holes 128 may correspond to the diameter of various fasteners that will be driven therethrough. Accordingly, the diameters of holes 128 may vary from one hole to the next depending on factors such as the patient's bone structure or the location of the fracture. Each hole 128 defines an axis extending therethrough. Each hole axis may be parallel to the other hole axes or may be angularly offset therefrom. As such, different fasteners may extend through holes 128 at different angles relative to each other. In some circumstances, holes 128 are angled such that fasteners extending therethrough have a trajectory that passes next to bone plate 108 on either the anterior or posterior side. Holes 128 may have internal threading or other retainment features to secure fasteners extending therein.

Fasteners 124 extending through holes 128 of intramedullary nail 104 may be any fastener known in the art, such as plunger screws. Further disclosure related to plunger screws is found in U.S. Patent App. No. 63/334,883, the disclosure of which is incorporated by reference herein. Nonetheless, fasteners may have various head, shank, and tips (not shown) depending on particular applications. Further, fasteners 124 may have various thread patterns across its head, shank, and tip depending on the particular application at hand (e.g., linking and non-linking fasteners).

FIGS. 1-2 illustrate a targeting block 110 according to one embodiment of the present disclosure. Targeting block 110 extends along a longitudinal axis and may define a similar profile to bone plate 108. Thus, in the preferred embodiment described herein, targeting block 110 is designed to be implemented with bone plate 108. In other embodiments, targeting blocks with other geometries may be used for different bone plate applications. As such, targeting block 110 may define a shape substantially similar to the shape of the underlying bone plate.

Targeting block 110 is elongated and extends from a superior end 130 to an inferior end 132. An inner surface 134 of targeting block 110 is configured to face and contact outer surface 120 of bone plate 108. Inner surface 134 is contoured to substantially match the contouring of bone plate 108 to minimize a gap between targeting block 110 and bone plate 108. Apart from pins 112, inner surface 132 of targeting block 110 may be substantially smooth or may include a textured surface, such as a textured coating or a roughened finish, to enhance the grip between targeting block 110 and bone plate 108. The superior end 114 and inferior end 116 of targeting block 110 may terminate at a blunt edge or may taper to a point. Any endpoint or side region of targeting block 110 is preferably smooth to minimize the possibility of the surrounding tissue snagging or otherwise being damaged by targeting block 110.

Targeting block 110 includes at least one bore (not shown) extending entirely through its thickness defined by the inner surface 134 and outer surface 136. The bore includes a plurality of bores spaced apart from each other in a pattern that substantially aligns with the pattern of holes of the underlying bone plate 108. As such, the bores of targeting block 110 preferably align with and are coaxial with at least some of the holes 122 of bone plate 108. The bores may be cylindrical such that a fastener extending therethrough can translate along the central longitudinal axis of the bore. Alternatively, for a slotted or variable angle hole 122 in bone plate 108, the corresponding bore of targeting block 110 may be slotted or conical to allow a fastener to extend therethrough along a plurality of different axes.

Continuing with the same embodiment, FIGS. 1-2 depict various pin attachments between targeting block 110 and bone plate 108. Inner surface 134 of targeting block 110 includes at least one pin 112 configured to be received within a hole 122 of bone plate 108. Preferably, pin 112 includes at least two pins 112 spaced apart from one another to prevent rotation of targeting block 110 relative to bone plate 108 when connected and ensure the bores align with holes 122. It is envisioned that any number of pins 112 may be implemented to attach targeting block 110 to bone plate 108.

Pin 112 extends from inner surface 134 of targeting block 110 away from targeting block 110. Depending on the bone plate being utilized, pin 112 may extend orthogonally away from inner surface 134 or at an oblique angle relative to the inner surface 134, as long as pin 112 may be inserted into a corresponding hole in bone plate 108. Pin 112 may have any cross-sectional shape known in the art. As depicted, pin 112 is cylindrical with a circular cross-section. In other embodiments, pin 112 may be rectangular with a square cross section. In a different embodiment, pin 112 may have a unique shape that acts as a key with a unique hole of the bone plate. The keyed arrangement may ensure that the targeting block 110 may only attach to the bone plate in one correct orientation, thus acting as a poka-yoke.

Pin 112 is elongated and extends along a longitudinal axis. In a preferred embodiment, pin 112 has a length longer than the thickness of bone plate 108 to allow pin 112 to extend through bone plate 108 and penetrate the underlying bone and/or contact an underlying fastener anchored in the cortical region of bone. In another embodiment, pin 112 may have a length less than the thickness of bone plate 108, thereby allowing pin 112 to rest in an indentation of bone plate 108 without passing entirely through bone plate 108.

Pin 112 is configured to engage a hole of bone plate 108. Hole 122 may be a hole configured to receive a fastener, or it may be a separate hole (not shown) configured to receive a pin rather than a fastener. Such a hole may have a diameter that corresponds to a pin diameter and may be smooth and lack threads or other retention features. In other embodiments, pin 112 can interact with a hole in bone plate 108 that is dedicated only for use with pin 112. In an alternative embodiment, pin 112 includes a spring (not shown) that biases pin 112 outward away from targeting block 110. The spring may include helical coils positioned around a longitudinal axis of pin 112 or the like. The spring may assist a user with locating pin 112 within a hole 122 of bone plate 108 by creating a tactile response when the pin engages the hole. Such a response could be a clicking sound or other response that alerts an operator the pin is positioned within a hole.

Figure 5:
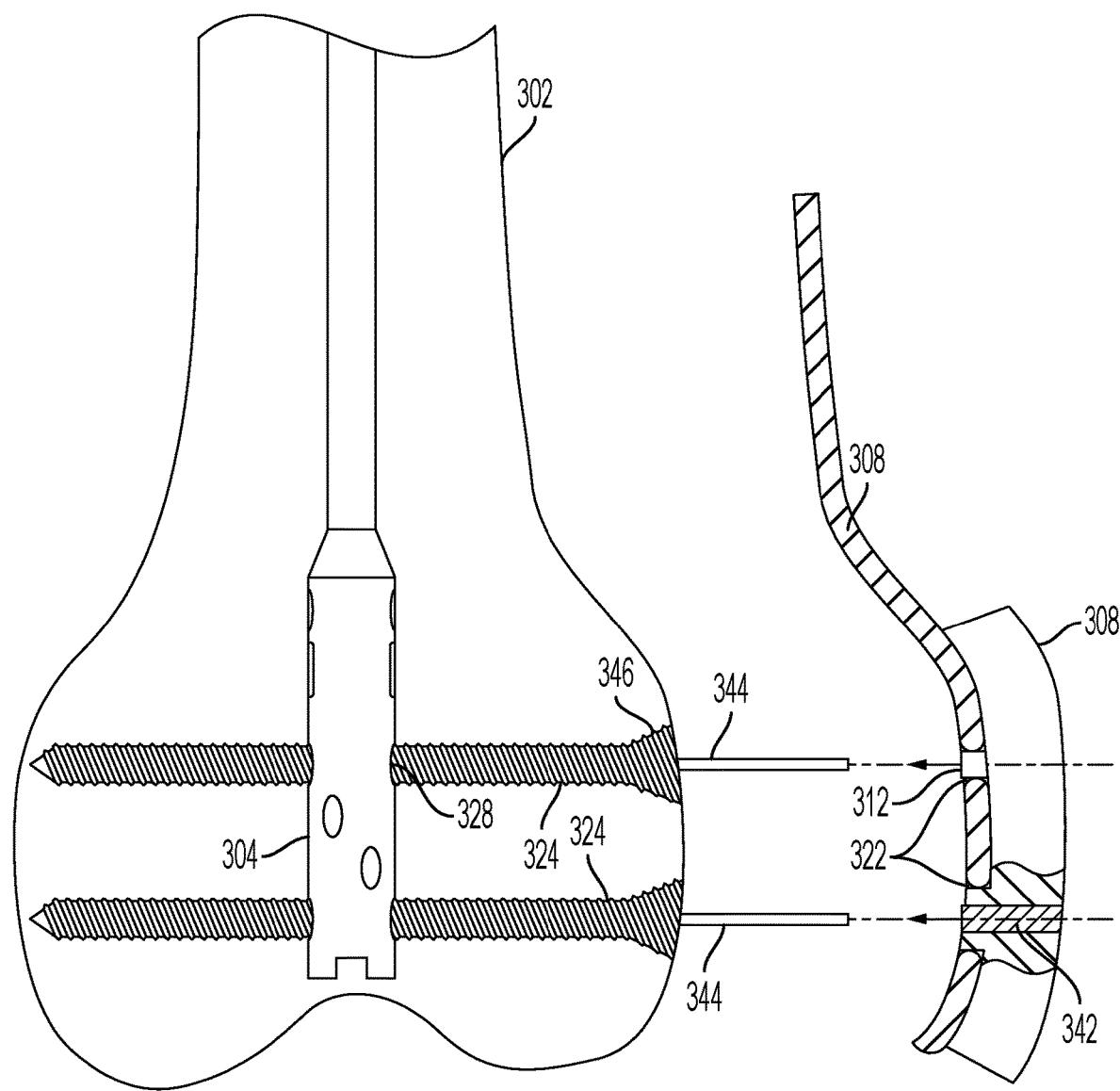
FIG. 5 is a side view of a partial cross-section of another embodiment of a fracture fixation system.
Figure 6:
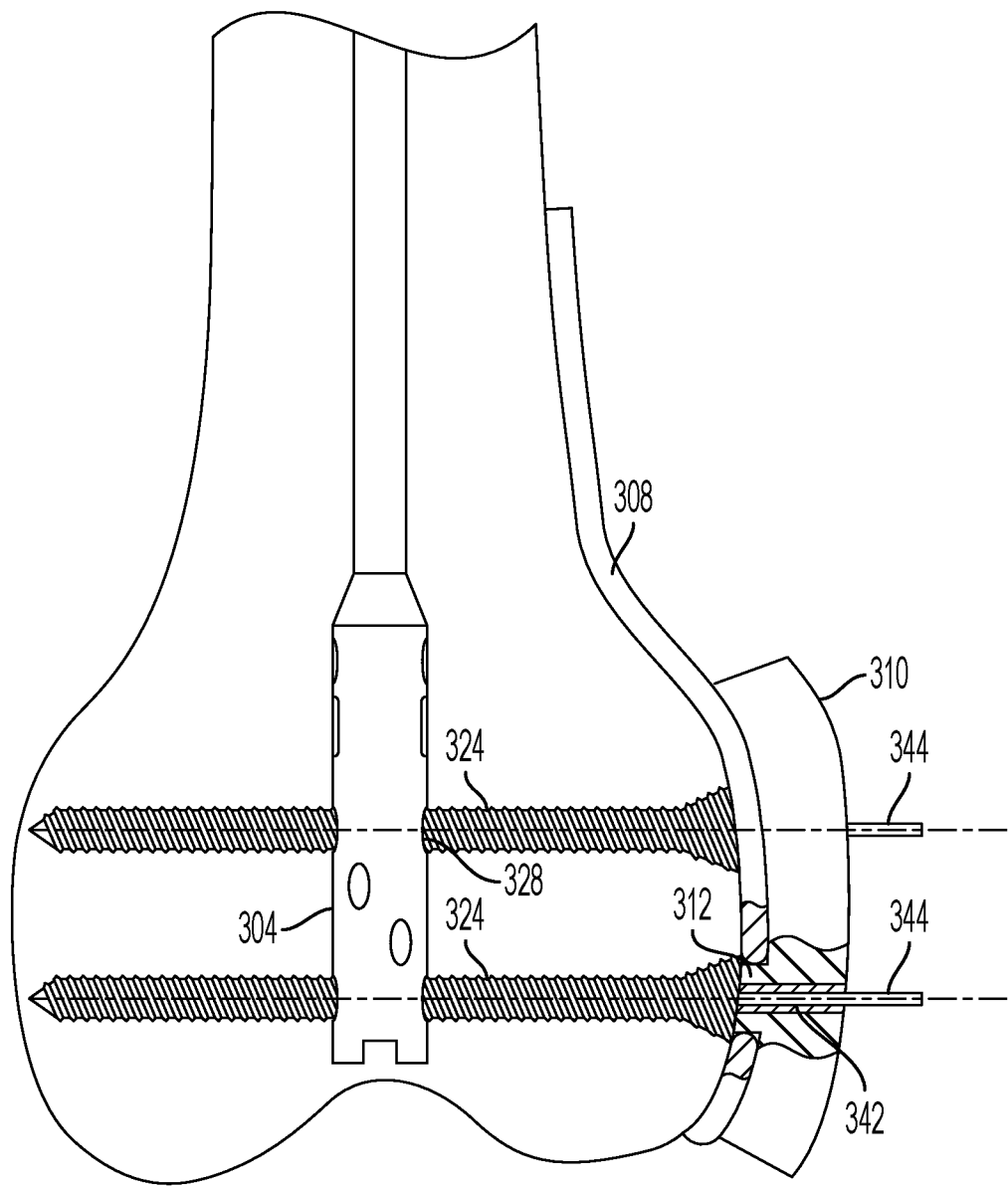
FIG. 6 is a side view of the partial cross-section of the fracture fixation system of FIG. 5 in an implanted configuration.
Figure 7:
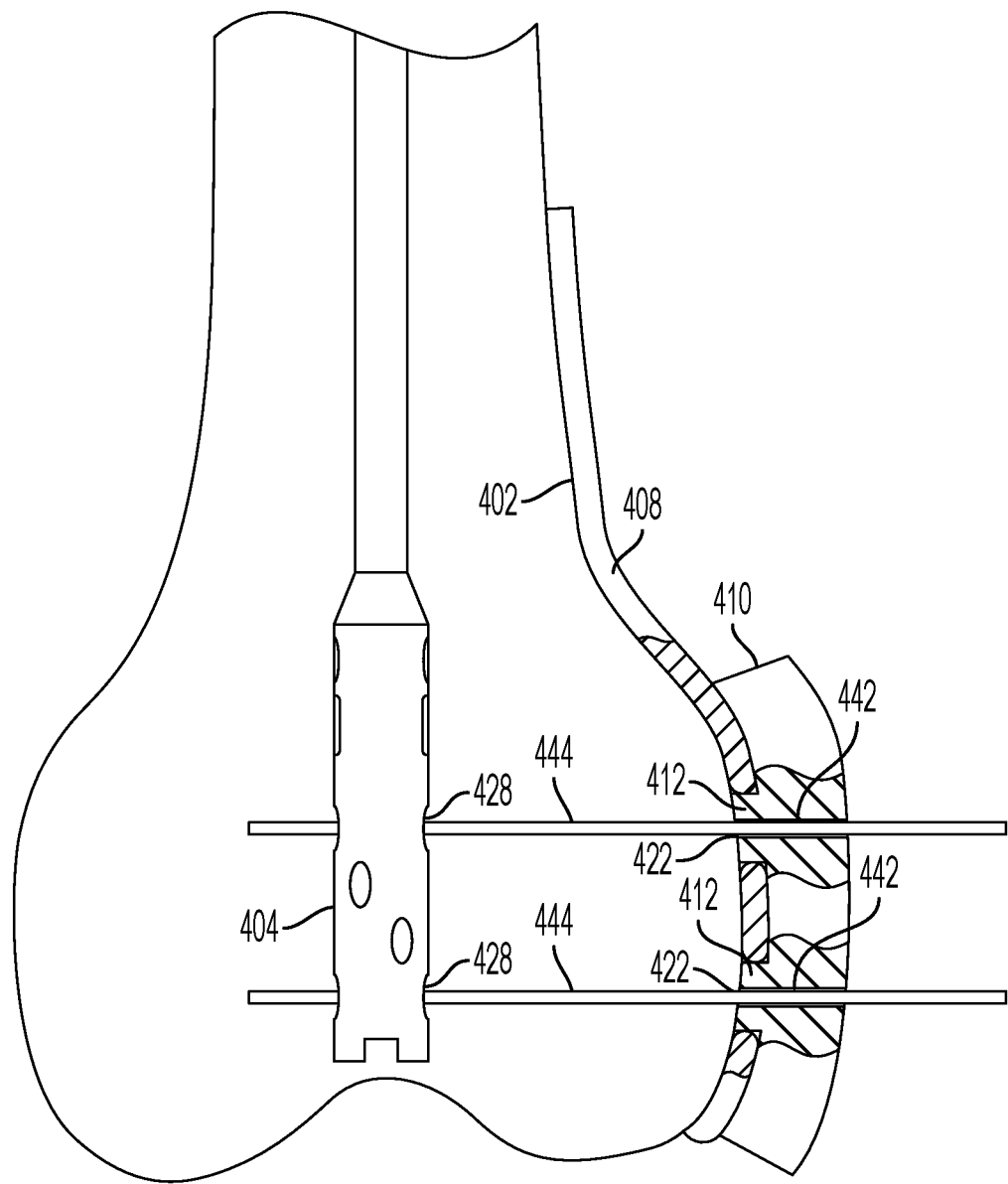
FIG. 7 is a side view of a partial cross-section another embodiment of a fracture fixation system.

FIGS. 5-7 depict an embodiment of the fracture fixation system 300 in which pin 312 is cannulated to allow a guide wire, such as k-wire 344, to pass therethrough. In such an embodiment, k-wire 344 may be passed through a bore of targeting block 308, cannula 342 of pin 312, and hole 322 of bone plate 308. K-wire 344 may then be inserted through the bone and through a hole 328 of intramedullary nail 304. Once inserted, bone plate 108 and targeting block 110 may translate along k-wire 344 as a unit or as separate components to contact the bone.

Pin 112 may be monolithically formed with targeting block 110 or may be a separate component attachable to the targeting block 110. Depending on the material of targeting block 110, pin 112 and targeting block 110 may be formed through additive manufacturing processes, such as 3D printing or other manufacturing processes, such as molding, extrusion, or the like. Pin 112 may be formed from a variety of materials known in the art. In some embodiments, pin 112 may be at least one of a polymeric material, titanium, and stainless steel. Additionally, radiolucent materials may be implemented to offer a benefit of non-impaired intra-op visibility.

A method of attaching a targeting block to a bone plate and to the underlying bone is described herein and is depicted in FIGS. 1-2. The method described herein begins in a configuration depicted in FIG. 1 in which bone plate 108 and targeting block 110 are removed from the bone 102. An intramedullary nail 104 is first inserted into a medullary canal of a bone using standard insertion methods known in the art. Intramedullary nail 104 may have a plurality of pre-drilled holes 128 arranged in a pattern. At least one unlinked fastener 124 may then be driven into the bone and through holes 128 of intramedullary nail 104. Head 146 of unlinked fastener may be countersunk into the cortical region of bone to avoid interference with bone plate 108 when bone plate 108 is placed against the bone. Head 146 of unlinked fastener may define an opening 148 for receiving pin 112 of targeting block 110.

Bone plate 108 is then prepared for contacting the bone in an implanted configuration illustrated in FIG. 2. Bone plate 108 includes at least one hole for receiving a fastener and at least one pin hole 122 for receiving a pin 112 of a targeting block 110. In certain embodiments, pin hole 122 can also accommodate a fastener. Targeting block 110 includes at least one bore configured to align with a hole of bone plate 108 and at least one pin 112 for attaching to bone plate 108. Pin 112 of targeting block 110 may be inserted through hole 122 of bone plate 108 before bone plate 108 is placed against the bone. Alternatively, pin 112 of targeting block 110 may be placed through hole 122 of bone plate 108 while bone plate 108 is placed against the bone. Each of pins 112 are preferably placed through holes 122 of bone plate 108 simultaneously to uniformly minimize a gap between targeting block 110 and bone plate 108 and to prevent targeting block 110 from rotating relative to bone plate 108. Targeting block 110 may be translated toward bone plate 108 until inner surface 134 of targeting block 110 is substantially flush with outer surface 120 of bone plate 108.

Continuing with this embodiment, pins 112 are maneuvered to extend entirely through holes 122 of bone plate 108 such that pins 112 contact the underlying bone 102 or engage the openings 148 within heads 146 of unlinked fasteners 124 to provide alignment between the bone plate 108 and the bone 102. As such, the pattern of holes of targeting block 110 may be predetermined based upon the location of unlinked fasteners 124.

Once targeting block 110 is securely attached to bone plate 108 and to the underlying bone, an operator may determine which bores of the bone plate require pilot holes to be drilled therein to receive a fastener. This determination may be patient-specific and may be based on factors such as fracture type, bone density, etc. Once the determination is made, an operator may drill pilot holes through the bores of targeting block 110 and through the holes of bone plate 108 into the underlying bone. Pilot holes may be drilled through fixed-angle holes with predetermined axes, or pilot holes may be drilled in variable-angle holes along an optimal axis for the given application. Because of the alignment between targeting block 110, bone plate 108, bone 102, and unlinked fasteners 124, pilot holes drilled through targeting block 110 and bone plate 108 are aligned to either pass through holes 128 of intramedullary nail 104 or to pass adjacent to intramedullary nail 104 without contacting it.

After pilot holes have been drilled, an operator may prepare fasteners, such as bone screws, for insertion. The fasteners may be selected based on various factors, such as type of fracture, length required, and thread type. Once selected, an operator may drill the fasteners through the bores of targeting block 110 and through the holes of bone plate 108 into the underlying bone. The fasteners may be drilled into either fixed-angle holes or variable-angle holes depending on the application. Certain fasteners may extend through both the holes of bone plate 108 and through holes 128 of intramedullary nail 104. Other fasteners (not shown) may extend through holes of bone plate 108 and into the underlying bone without contacting intramedullary nail. Fasteners may be driven through the holes of bone plate 108 until the fastener head engages the contouring of the hole to lock the fastener in place and prevent it from backing out.

Figure 3:
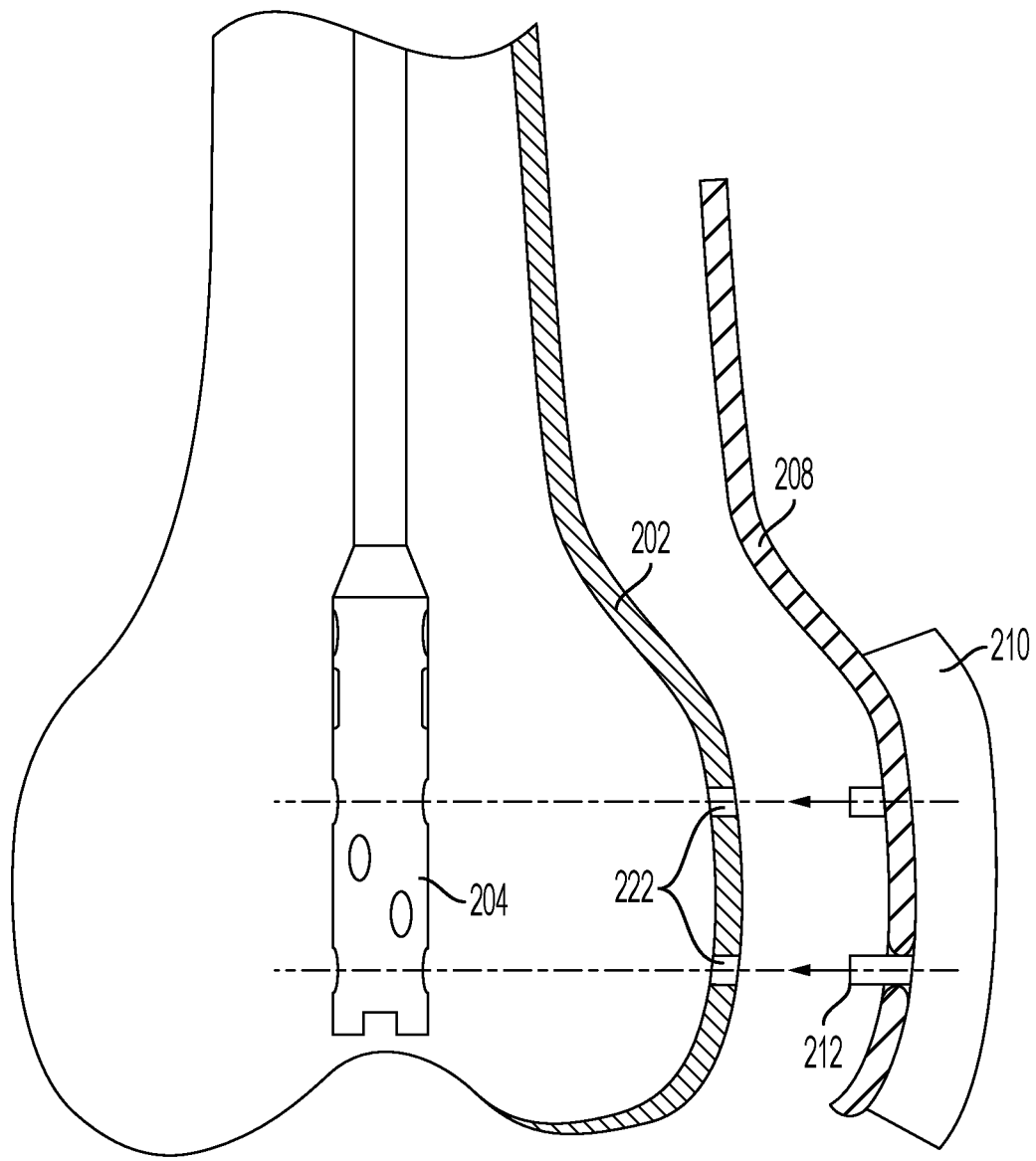
FIG. 3 is side view of a partial cross-section of another embodiment of a fracture fixation system.
Figure 4:
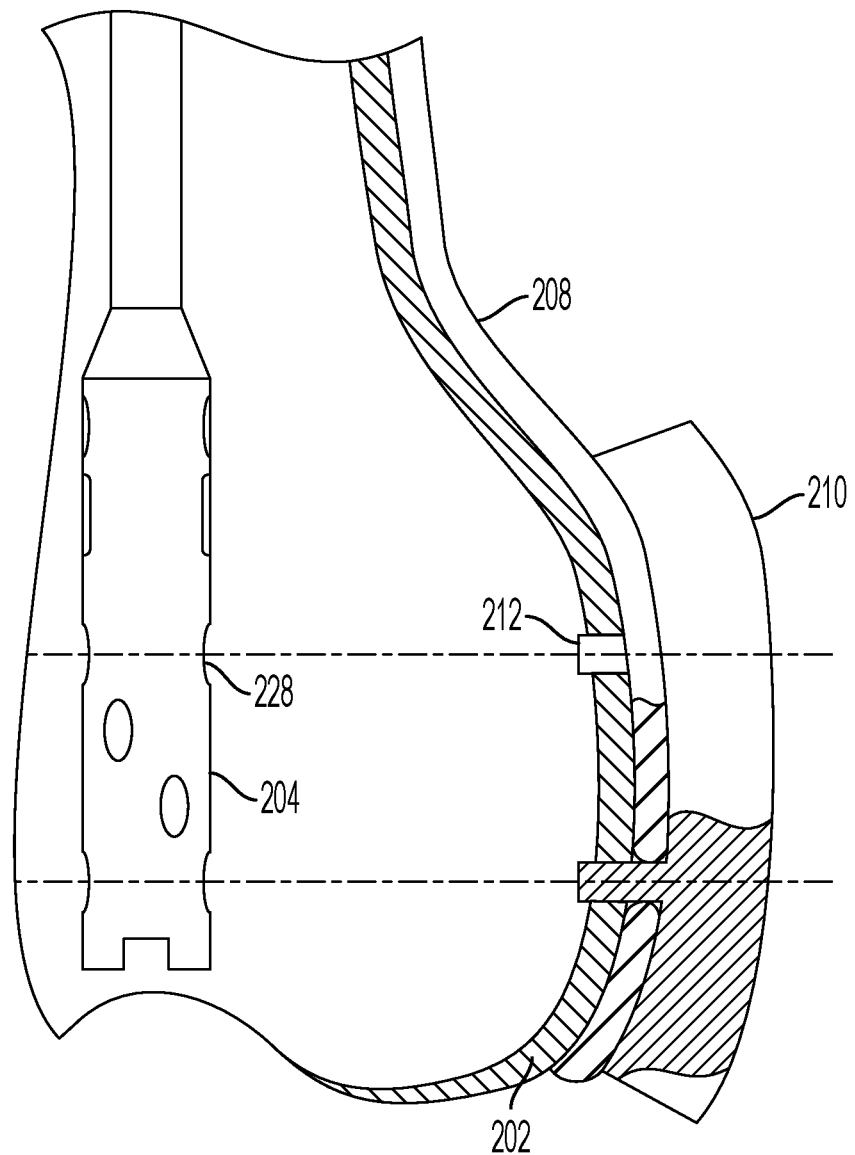
FIG. 4 is a side view the partial cross-section of the fracture fixation system of FIG. 3 in an implanted configuration.

FIGS. 3-4 illustrate another embodiment of attaching a targeting block to a bone plate and a bone. In this method, targeting block 210 and bone plate 208 are similar to targeting block 110 and bone plate 108, and therefore like elements are referred to with similar numerals within the 200-series of numbers. Intramedullary nail 204 may be first inserted into a medullary canal of a bone using similar techniques to those described for intramedullary nail 104. Unlike the previous method, this method does not rely on the use of unlinked fasteners that are inserted prior to the bone plate such that the fastener head is sunk into a cortical region of bone. Pins 212 of targeting block 210 have a length greater than the thickness of bone plate 208. Accordingly pins 212 can be inserted through the holes 222 of bone plate 208 and penetrate the underlying cortical region of bone 202 when the system is transitioned from a removed configuration (FIG. 3) to an implanted configuration (FIG. 4) and when bone plate 208 is placed against the bone 202. The location of contact between pins 212 and bone 202 may be used as a reference location about which targeting block 210 is based to ensure proper alignment of pilot holes and fasteners drilled through targeting block 210 and bone plate 208 in relation to intramedullary nail 204. Pins 212 ensure such an alignment and further ensure that the trajectory of pilot holes and fasteners driven through targeting block 210 and bone plate 208 is optimal for a given fracture. Alternatively, an operator may first drill a hole through the cortical region of bone before targeting block 210 and bone plate 208 are placed against the bone. As such, pins 212 may be positioned within the drilled hole to ensure that targeting block 210 is positioned about a desired reference point.

FIGS. 5-6 illustrate another embodiment of attaching a targeting block to a bone plate and a bone. In this method, targeting block 310 and bone plate 308 are similar to targeting block 110 and bone plate 108, and therefore like elements are referred to with similar numerals within the 300-series of numbers. Intramedullary nail 304 may be first inserted into a medullary canal of a bone using similar techniques to those described for intramedullary nail 104. Unlinked fasteners 324 may also be inserted into the bone using similar techniques to those described for unlinked fasteners 124. Unlike fasteners 124, fasteners 324 are cannulated. Pins 312 of targeting block 310 are cannulated to allow a k-wire 344 or other guidewire to pass therethrough a cannula 342. As such, k-wire 344 may be fed through a bore of targeting block 310, cannula 342 of pin 312, and hole 322 of bone plate 308. K-wire 344 may then be fed through the cannula of unlinked fastener 324. After the k-wire 344 has been inserted in the removed configuration of FIG. 5, the targeting block 310 and bone plate 308 may be slid along the k-wire 344 until the bone plate 308 contacts the underlying bone in an implanted configuration of FIG. 6. In the implanted configuration, pins 312 ensure proper alignment between targeting block 310 and bone plate 308 such that pilot holes and fasteners driven therethrough will extend through holes 328 of intramedullary nail 304 or extend adjacent intramedullary nail 304 without contacting it, if desired. Once targeting block 310 and bone plate 308 are in place, an operator may drill pilot holes and drive fasteners through targeting block 310 and bone plate 308 using techniques similar to method 150.

FIG. 7 illustrates another embodiment of attaching a targeting block to a bone plate and a bone. In this method, targeting block 410 and bone plate 408 are similar to targeting block 110 and bone plate 108, and therefore like elements are referred to with similar numerals within the 400-series of numbers. Intramedullary nail 404 may be first inserted into a medullary canal of a bone using similar techniques to those described for intramedullary nail 104. Rather than implementing unlinked fasteners, this method allows an operator to pass k-wire 444 directly though the bone and through a hole 428 of intramedullary nail 404.

Continuing with this embodiment, after intramedullary nail 404 has been inserted, an operator may pass k-wire 444 through the bone such that a first end of k-wire 444 is passed through a hole 428 of intramedullary nail 404. K-wire 444 may then act as a reference point upon which bone plate 408 and targeting block 410 are based. The second end of k-wire 444 may then be passed through a hole 422 of bone plate 408 and through cannulated pin 412 of targeting block 410. Once k-wire 444 has been inserted through each component, targeting block 410 and bone plate 408 may be joined together and translate along k-wire 444 until bone plate 408 contacts the underlying bone 402.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to a further advantage. Any reference signs in the claims should not be construed as limiting the scope.

The invention claimed is:

1. A method for aligning an aiming block with respect to a bone comprising:
   driving a bone screw into a bone to pass a tip of the bone screw through a hole of an intramedullary nail and to anchor a head of the bone screw in a cortical region of the bone;
   inserting a pin extending from a surface of an aiming block through a hole of a bone plate; and
   contacting the pin against the head of the bone screw to align the hole of the bone plate with the head of the bone screw.

2. The method of claim 1, further comprising inserting the intramedullary nail into a medullary canal of a bone.

3. The method of claim 1, wherein the contacting step includes inserting the pin into a recess within the head of the bone screw.

4. The method of claim 2, wherein the contacting step further comprises pressing the pin partially into the aiming block by compressing a spring disposed between the pin and aiming block.

5. The method of claim 1, further comprising driving a second bone screw into the bone to pass a tip of the second bone screw through a second hole of the intramedullary nail and to anchor a head of the second bone screw in the cortical region of the bone.

6. The method of claim 5, further comprising inserting a second pin extending from the surface of the aiming block through a second hole of the bone plate.

7. The method of claim 6, wherein the contacting step includes placing the pin against the head of the bone screw and the second pin against the head of the second bone screw.

8. The method of claim 1, wherein the driving step includes driving the head of the bone screw into a countersunk recess within the bone.

9. A method of aligning an aiming block with respect to a bone comprising:
   drilling a hole in a cortical region of a bone;
   inserting a pin extending from a surface of an aiming block through a hole of a bone plate; and
   locating the pin within the hole in the cortical region of the bone.

10. The method of claim 9, further comprising inserting an intramedullary nail into a medullary canal of the bone.

11. The method of claim 10, wherein the locating step includes locating the pin such that a central longitudinal axis of the pin aligns with a central longitudinal axis of a hole of the intramedullary nail.

12. The method of claim 10, further comprising removing the bone plate and the aiming block from the bone.

13. The method of claim 12, further comprising inserting a bone screw through the bone such that a head of the bone screw sits in a recess formed by the pin and a tip of the bone screw extends through the hole of the intramedullary nail.

14. The method of claim 13, further comprising placing the bone plate over the bone such that the head of the bone screw sits beneath the hole of the bone plate.

15. A method for aligning an aiming block with respect to a bone comprising:
   inserting an intramedullary nail into a medullary canal of a bone;
   inserting a k-wire into the bone and through a hole of the intramedullary nail;
   placing a hole of a bone plate and an aligned hole extending through an aiming block over an end of the k-wire; and
   guiding the bone plate and the aiming block along the k-wire to contact an inner surface of the bone plate to the bone.

16. The method of claim 15, further comprising inserting a second k-wire into the bone and through a second hole of the intramedullary nail.

17. The method of claim 16, wherein the placing step further comprises placing a second hole of the bone plate and an aligned second hole extending through the aiming block over an end of the second k-wire.

18. The method of claim 17, wherein the guiding step includes guiding the bone plate and the aiming block along the k-wire and the second k-wire to contact the inner surface of the bone plate to the bone.

19. The method of claim 15, further comprising inserting a cannulated bone screw into the bone to pass a tip of the cannulated bone screw through the hole of the intramedullary nail and to anchor a head of the cannulated bone screw into a cortical region of the bone.

20. The method of claim 19, wherein the step of inserting the k-wire includes inserting the k-wire through the cannulated bone screw.

* * * * *